Figure 1:
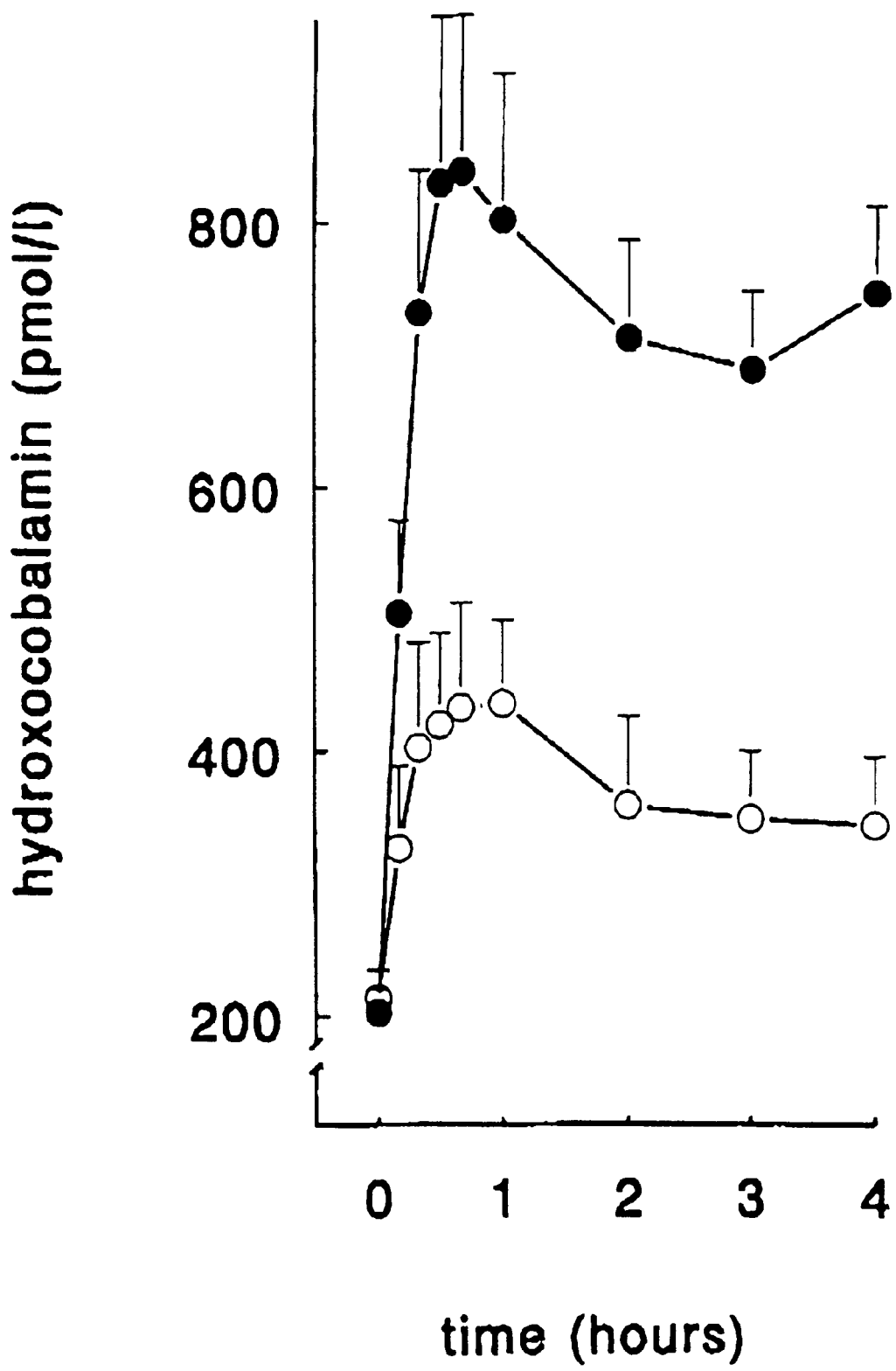

United States Patent [19]
Merkus

[11] Patent Number: 5,925,625
[45] Date of Patent: Jul. 20, 1999

[54] PHARMACEUTICAL COMPOSITION FOR THE INTRANASAL ADMINISTRATION OF HYDROXOCOBALAMIN

[76] Inventor: Franciscus W. H. M. Merkus, Grootreesdijk 26, B-2460 Kasterlee, Belgium

[21] Appl. No.: 09/000,729

[22] Filed: Dec. 30, 1997

Related U.S. Application Data

[63] Continuation-in-part of application No. 08/663,240, filed as application No. PCT/EP94/01567, May 13, 1994, Pat. No. 5,801,161.

[51] Int. Cl.⁶ .................................................... A61K 31/70
[52] U.S. Cl. ................................................................. 514/52
[58] Field of Search ................................................ 514/52

[56] References Cited

U.S. PATENT DOCUMENTS 3,903,253   9/1975   Rolland .

FOREIGN PATENT DOCUMENTS

WO-A8605987   10/1986   WIPO .
WO-A8605988   10/1986   WIPO .

*Primary Examiner*—Raymond Henley, III
*Attorney, Agent, or Firm*—Jones, Day, Reavis & Pogue

[57] ABSTRACT

A method and composition are disclosed for the prophylaxis and treatment of vascular headaches such as migraine headaches and cluster headaches. The method comprises the intranasal administration of a pharmaceutical composition comprising one or more hydroxocobalamin compounds in a total concentration above 1% (w/w), said composition having a viscosity less than 1000 cP.

19 Claims, 2 Drawing Sheets

PHARMACEUTICAL COMPOSITION FOR THE INTRANASAL ADMINISTRATION OF HYDROXOCOBALAMIN

This is a continuation-in-part of Ser. No. 08/663,240, having an acceptance date under 35 U.S.C. § 371 of Jun. 17, 1996, now U.S. Pat. No. 5,801,161, and which is a United States National Filing of International Application No. PCT/EP94/01567, having an international filing date of May 13, 1994.

The invention is related to a pharmaceutical composition for the intranasal administration of hydroxocobalamin, a substance from the vitamin B12 family.

Vitamin B12 has been first isolated in 1948 and since that time it is widely used in therapeutically active drugs in the treatment of pernicious anemia and other vitamin B12 deficiency disorders. These diseases are mainly caused by an inadequate absorption of vitamin B12 from the gastrointestinal tract.

Vitamin B12 occurs in the human body as methylcobalamin, adenosylcobalamin, hydroxocobalamin and cyanocobalamin. Only cyanocobalamin and hydroxocobalamin are used in the treatment of patients.

Oral, sublingual as well as nasal administration of vitamin B12 appeared to be ineffective treatments and therefore administration by intramuscular injection is the only satisfactory and medically accepted therapy up to now. However, intramuscular injections of vitamin B12 have many disadvantages, especially because this drug is often administered to older people. Such people may have reduced muscle mass or are atrophic, so that repeated injections are inconvenient and painful, and also require doctor's visits. Maintenance therapy with vitamin B12 means at least monthly injections and must be continued for life.

Already in 1953 Monto et al (Am. J. Med. Sci., 1953, Vol. 225, pages 113–119) published a study related to an alternative route for administering vitamin B12, i.e. nasal inhalation aiming at deposition of therapeutically active material in the lungs. Cyanocobalamin in lactose powder and in physiological saline solutions, containing 15 to 200 $\mu$g crystalline cyanocobalamin per ml, were used for nasal inhalation. The results of this investigation of vitamin B12 administration by inhalation were reported as encouraging, but constituting only preliminary observations regarding the efficiency of inhalation crystalline cyanocobalamin treatment of pernicious anemia. The publication mentioned that intranasal B12 drops and dust, as routes of administration, were also under investigation by that time.

Israëls and Shubert (The Lancet, Feb. 13, 1954, pages 341–343) stressed the disadvantage of having no alternative for the intramuscular administration of vitamin B12 and published some experiences supporting some of the findings of Monto et al (1953), i.e. vitamin B12 seems to be therapeutically effective when administered by inhalation as a powder.

In 1954 Monto et al published further experiences, with nasal inhalation and installation of crystalline vitamin B12 (Arch. of Int. Med. 93, 1954, pages 219–230). They reported a good hemopoietic effect after nasal administration of cyanocobalamin in lactose powder or in a dose of 100 $\mu$g per ml in a saline solution. Although the therapy was characterized as being not only effective but safe and economical, there was no follow up or any factual medical use of the therapy in the subsequent decennia. Since the urgent need for an alternative administration route continued to exist, apparently, the conclusions in the publications were too optimistic.

Other proposals for intranasal administration of vitamin B12 are described in PCT/US86/00665 and PCT/US 86/00793. Both proposals are based on the assumption that previous experiments failed, because of the fact that the administered cyanocobalamin, in a solution or powder, did not remain in the nasal cavity, but passes the nose to the throat or lungs. To solve this problem, both patent applications propose that the nasal formulation should stay for a much longer time in the nasal cavity. To obtain this longer residence time the formulation is administered in the form of an aerosol (PCT/US/86/00665) or the formulation should possess an enhanced viscosity, above 2500 cP (PCT/US/86/00793). This should give a consistent, continuous and uniform absorption of vitamin B12. A concentration from 0.05% to 1% by weight based on the total weight is described as typical concentrations of vitamin B12 in the compositions of both patent applications.

Extensive investigations have been carried out by applicant into the mechanism of the nasal absorption through the nasal epithelium of hydroxocobalamin and cyanocobalamin. For that purpose both substances were administered nasally in isotonic aqueous solutions to human volunteers. The investigations have lead to the new insight into the underlying mechanism of the nasal absorption of vitamin B12.

For the nasal absorption of vitamin B12, the longer nasal residence time of the formulation or the amount or volume of the formulation are of no or minor importance. The extent of the nasal absorption of vitamin B12 is mainly and principally governed only by the concentration of vitamin B12 in the nasal formulation.

A high and efficient intranasal absorption of vitamin B12 is advantageous in medical therapy, and can be obtained only by using hydroxocobalamin, which shows a significant higher solubility in water than cyanocobalamin. Only with hydroxocobalamin a superior nasal composition in an aqueous medium can be produced with by far the highest concentration of vitamin B12 and consequently a much more efficient nasal absorption of vitamin B12. Such a nasal formulation can be taken less frequently by patients, making the therapy much easier and less expensive.

DESCRIPTION AND EXAMPLE

The following experiments were conducted in 6 healthy male volunteers to establish the bioavailability, which means the extent and rate of absorption, of a nasally administered vitamin B12. For the study only non-smokers were selected, because in smokers serum levels of vitamin B12 can be found, which deviate from normal levels. Serum levels were measured by radioimmunoassay and expressed in pMol/l.

The results of the first experiment are summarized in table 1.

TABLE 1

Vitamin B12 serum concentration in 6 volunteers after nasal administration of hydroxocobalamin in an isotonic aqueous solution.

dose: 500 $\mu$g hydroxocobalamin HCl
volume: 100 $\mu$l
concentration: 500 $\mu$g/100 $\mu$l = 500 $\mu$g/100 mg = 0.5%

| Time after administration (minutes) | Vit B12 pMol/l | Standard deviation (n = 6) |
| --- | --- | --- |
| 0 | 214 | 21 |
| 10 | 328 | 61 |
| 20 | 403 | 79 |
| 30 | 420 | 69 |
| 40 | 433 | 71 |
| 60 | 436 | 63 |
| 120 | 360 | 66 |
| 180 | 350 | 50 |
| 240 | 345 | 51 |

The experiment as described in Table 1, was repeated with nasal administration of 500 $\mu$g cyanocobalamin. The formulations were also tested as aerosol and with formulations containing thickening agents like methylcellulose 400 mPas 1–2% and hydroxypropylmethylcellulose 4000 mPas 1%. None of the formulations gave a result which was significantly different from the results as listed in Table 1.

From these experiments we have drawn the conclusion, that

- the absorption of hydroxocobalamin and cyanocobalamin in the human nose takes place between 0–60 minutes after nasal administration and the maximum serum level (Cmax) is reached between 30–60 minutes (Tmax); and that—the nasal administration of the formulations as aerosol, as described in PCT/US86/00665, or the formulation containing thickening agents, as described in PCT/US 86/00793, does not, or insignificantly, influence or modify the rate and extent of the nasal absorption of vitamin B12.

Continued investigations were carried out into the real mechanism of the nasal absorption of cyanocobalamin and hydroxocobalamin.

The following surprising results were obtained and the following conclusions were drawn:

- the extent of nasal absorption of vitamin B12, is mainly governed by the level of the concentration of vitamin B12 in solubilized form, which is applied to the nasal mucosa.

- the most effective concentrations of vitamin B12 in the formulations for nasal administration are higher than 1%. The maximal concentration, that can be reached with cyanocobalamin is about 1%. Concentrations above 1% can only be obtained with hydroxocobalamin, because its good solubility in water. The solubility of hydroxocobalamin substances can be as high as 10%, which means that up to about 10 times more vitamin B12 per unit of volume can be administered and subsequently absorbed nasally, when hydroxocobalamin is used.

This surprising finding is illustrated in Table 2, showing the nasal absorption of hydroxocobalamin in 6 volunteers, after nasal administration of hydroxocobalamin in a concentration of 2%, which is a much higher concentration than maximally possible with cyanocobalamin. From the results it appears, that the absorption efficiency increases with the increasing concentration in the nasal formulation. In FIG. 1 the results from Table 1 and Table 2 are illustrated. The open circles represent the mean serum levels of hydroxocobalamin 0.5% (500 µg/100 µl) and the closed circles of hydroxocobalamin 2% (1500 µg/75 µl). The vertical bars represent the standard deviation.

The rise in Cmax after nasal administration of 2% hydroxocobalamin is several times higher than after administration of the 0.5% concentration. The concentration of hydroxocobalamin appears to be of decisive importance for an efficient nasal absorption. A superior nasal absorption of vitamin B12 in therapy, can therefore, only be obtained by administration of a formulation containing a high concentration of hydroxocobalamin.

TABLE 2

Vitamin B12 serum concentration in 6 volunteers after nasal administration of hydroxocobalamin in an isotonic aqueous solution.

dose: 1500 µg hydroxocobalamin HCl
volume: 75 µl
concentration: 1500 µg/75 µl = 1500 µg/75 mg = 2%

| Time after administration (minutes) | Vit B12 pMol/l | Standard deviation (n = 6) |
|---|---|---|
| 0 | 203 | 18 |
| 10 | 504 | 71 |
| 20 | 731 | 109 |
| 30 | 830 | 124 |
| 40 | 839 | 116 |
| 60 | 802 | 110 |
| 120 | 712 | 75 |
| 180 | 688 | 59 |
| 240 | 746 | 67 |

According to the invention, the concentration of hydroxocobalamin in the nasal formulation is higher than 1%, preferably higher than 1.2%. The maximal solubility of hydroxocobalamin is about 10%, which is about 10× higher than can be reached with cyanocobalamin.

Nasal administration of the invented composition may take place according to any method, known from the pharmaceutical literature. It is also possible to use capsules, tampons or sponges, containing the hydroxocobalamin nasal composition.

According to the invention the nasal pharmaceutical composition contains hydroxocobalamin in a aqueous medium and the total composition possesses a low viscosity, less than 1000 cP, preferably below 100 cP.

The composition may also contain a number of excipients or additives, known from the pharmaceutical literature to be added to nasal formulations, such as preservatives, agents to adjust the pH or the osmolarity, surfactants, complexing agents, stabilizers and solubilizers.

Hydroxocobalamin in pharmaceutical formulations may be hydroxocobalamin, hydroxocobalamin HCl, sulphate, acetate and similar derivatives. In water hydroxocobalamin occurs in equilibrium with aquocobalamin. In pharmaceutical compositions the quality of the hydroxocobalamin should comply with the requirements of a Pharmacopoeia. In the experiments, presented in table 1 and 2, hydroxocobalamin according to the requirements of the British Pharmacopoeia 1988 has been used.

The applicant herein also has found that intranasal administration of hydroxocobalamin in accordance with the disclosed method is also effective in both the treatment and prophylaxis of vascular headaches, including migraine headaches, cluster headaches, and other known types of vascular headaches. While it was previously known that vascular headaches could be treated with vitamin B12, such treatments were limited by the fact that effective amounts of vitamin B12 could be administered only be intramuscular injection. The instant inventive method of intranasal administration of vitamin B12 allows a patient to self-administer vitamin B12 at dosage levels high enough to provide effective treatment and prophylaxis of vascular headaches.

The efficacy of the inventive method in the prophylaxis and treatment of vascular headaches is demonstrated by the following examples, each of which describes preliminary results obtained in ongoing studies.

EXAMPLE 3

Figure 2:
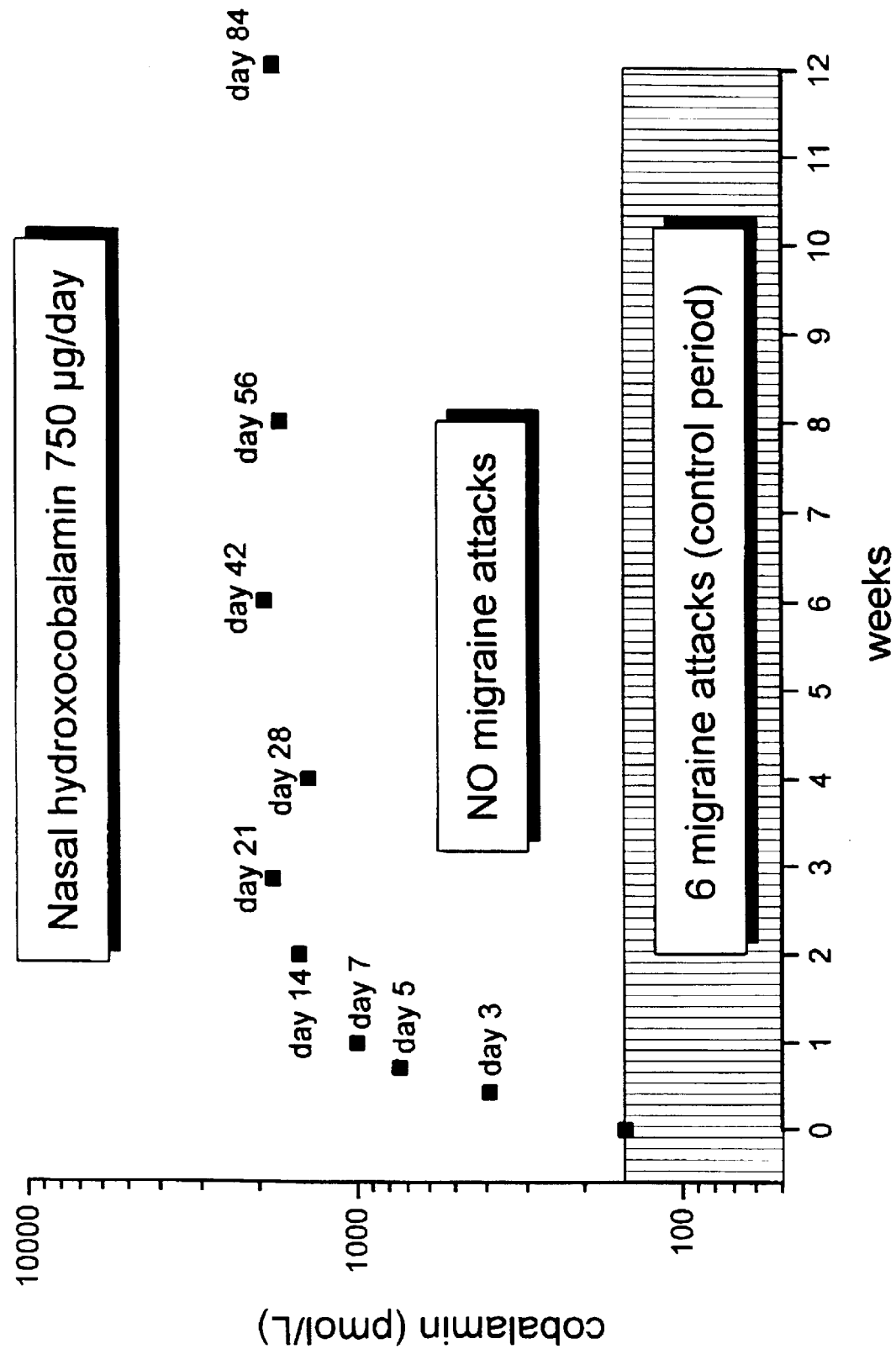

A first patient known to experience migraine headaches was monitored for twelve weeks without any treatment with vitamin B12 with to establish a control period. As shown in FIG. 2, during this first 12-week control period, the patient experienced six migraine headaches. Also during this control period, the level of cobalamin in the patient's blood plasma was determined to be between 100–200 pmol/L. Over the following 12 weeks, the patient received daily doses of 750 μg hydroxocobalamin administered intranasally as a single puff of 50 μl of a 1.5% hydroxocobalamin formulation having a viscosity less than 1000 cP. During this second 12-week period, this patient experienced no migraine headaches, i.e., the migraines were completely eliminated. Also during this second 12-week period, the level of cobalamin in the patient's blood increased to over 1000 pmol/L, as shown on the vertical logarithmic scale of FIG. 2.

EXAMPLE 4

A second patient who was experiencing the beginning of a migraine headache attack was treated with 5000 μg hydroxobalamin received as a single dose administered intranasally in a 100 μl puff of 5% hydroxocobalamin nasal formulation having a viscosity less than 1000 cP. The attack soon subsided and never developed into a full migraine headache.

EXAMPLE 5

A third patient who was experiencing severe cluster headaches was treated with 10000 μg hydroxocobalamin administered intranasally as two 100 μl puffs, one in each nostril, of a 5% hydroxocobalamin nasal formulation having a viscosity less than 1000 cP. The treatment was successful and the cluster headaches soon subsided.

The foregoing examples suggest that intranasal administration of hydroxocobalamin can be effective in the prophylaxis and treatment of vascular headaches. It will be appreciated that the hydroxocobalamin formulation useful in the treatment of vascular headaches will be formulated in accordance with the principles disclosed previously in this application, namely a total hydroxocobalamin concentration above 1% (w/w), and preferably in the range of 1.1–10% (w/w), the composition having a viscosity less than 1000 cP, and further optionally including one or more additives such as a preservative, an agent to adjust the pH, an agent to adjust the osmolarity, a surfactant, a complexing agent, a stabilizing agent, and a solubilizer. It further will be appreciated that the intranasal administration can be accomplished by means of a capsule, a unit dose vial, a nasal tampon, or a nasal sponge. The hydroxocobalamin used in the formulations for treating vascular headaches may be in the form of hydroxocobalamin, hydroxocobalamin hydrochloride, hydroxocobalamin sulphate, hydroxocobalamin acetate, and any other pharmaceutically acceptable hydroxocobalamin salt.

I claim:

1. A method of treating a vascular headache, the method comprising the intranasal administration of a pharmaceutical composition, said composition comprising one or more hydroxocobalamin compounds selected from the group consisting of hydroxocobalamin, hydroxocobalamin chloride, hydroxocobalamin sulphate, hydroxocobalamin acetate, and any other pharmaceutically acceptable hydroxocobalamin salt, dissolved in an aqueous solution in a total concentration above 1% (w/w), said composition having a viscosity of less than 1000 cP.

2. The method of claim 1 wherein the total concentration of said one or more hydroxocobalamin compounds is in the range of 1.1–10% (w/w).

3. The method of claim 1 wherein said composition further comprises one or more additives selected from a preservative, an agent to adjust the pH, an agent to adjust the osmolarity, a surfactant, a complexing agent, a stabilizing agent, and a solubilizer.

4. The method of claim 1 wherein said intranasal administration is accomplished by a means selected from a capsule, a unit dose vial, a nasal tampon, and a nasal sponge.

5. The method of claim 1 wherein said method is effective in the treatment of migraine headaches.

6. The method of claim 1 wherein said method is effective in the treatment of cluster headaches.

7. A method for the prophylaxis of vascular headaches, the method comprising the intranasal administration of a pharmaceutical composition, said composition comprising one or more hydroxocobalamin compounds selected from the group consisting of hydroxocobalamin, hydroxocobalamin chloride, hydroxocobalamin sulphate, hydroxocobalamin acetate, and any other pharmaceutically acceptable hydroxocobalamin salt, dissolved in an aqueous solution in a total concentration above 1% (w/w), said composition having a viscosity of less than 1000 cP.

8. The method of claim 1 wherein the total concentration of said one or more hydroxocobalamin compounds is in the range of 1.1–10% (w/w).

9. The method of claim 1 wherein said composition further comprises one or more additives selected from a preservative, an agent to adjust the pH, an agent to adjust the osmolarity, a surfactant, a complexing agent, a stabilizing agent, and a solubilizer.

10. The method of claim 1 wherein said intranasal administration is accomplished by a means selected from a capsule, a unit dose vial, a nasal tampon, and a nasal sponge.

11. The method of claim 1 wherein said method is effective in the prophylaxis of migraine headaches.

12. The method of claim 1 wherein said method is effective in the prophylaxis of cluster headaches.

13. In a method for the treatment or prophylaxis of vascular headaches by administration of vitamin B12, the improvement wherein the vitamin B12 is administered intranasally as a pharmaceutical composition, the composition comprising one or more hydroxocobalamin compounds selected from the group consisting of hydroxocobalamin, hydroxocobalamin chloride, hydroxocobalamin sulphate, hydroxocobalamin acetate, and any other pharmaceutically acceptable hydroxocobalamin salt, dissolved in an aqueous solution in a total concentration above 1% (w/w), said composition having a viscosity of less than 1000 cP.

14. The method of claim 13 wherein the total concentration of said one or more hydroxocobalamin compounds in the range of 1.1–10% (w/w).

15. The method of claim 13 wherein said composition further comprises one or more additives selected from a preservative, an agent to adjust the pH, an agent to adjust the osmolarity, a complexing agent, a stabilizing agent, and a solubilizer.

16. The method of claim 13 wherein said composition is effective in the treatment of migraine headaches.

17. The method of claim 13 wherein said composition is effective in the prophylaxis of migraine headaches.

18. The method of claim 13 wherein said composition is effective in the treatment of cluster headaches.

19. The method of claim 13 wherein said composition is effective in the prophylaxis of cluster headaches.

* * * * *